United States Patent
Okamoto et al.

(10) Patent No.: US 10,551,341 B2
(45) Date of Patent: Feb. 4, 2020

(54) GAS SENSOR

(71) Applicant: NGK INSULATORS, LTD., Nagoya-shi, Aichi (JP)

(72) Inventors: Taku Okamoto, Nagoya (JP); Nobuhiko Mori, Nagoya (JP); Yuki Nakayama, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 301 days.

(21) Appl. No.: 15/726,583

(22) Filed: Oct. 6, 2017

(65) Prior Publication Data

US 2018/0100828 A1 Apr. 12, 2018

(30) Foreign Application Priority Data

Oct. 12, 2016 (JP) ................... 2016-200798

(51) Int. Cl.
| G01N 27/407 | (2006.01) |
| G01N 27/30 | (2006.01) |
| G01N 27/419 | (2006.01) |

(52) U.S. Cl.
CPC ....... *G01N 27/4072* (2013.01); *G01N 27/301* (2013.01); *G01N 27/4075* (2013.01); *G01N 27/419* (2013.01); *G01N 27/4074* (2013.01)

(58) Field of Classification Search
CPC ............................................ G01N 27/403–41
See application file for complete search history.

(56) References Cited

U.S. PATENT DOCUMENTS

2011/0186431 A1* 8/2011 Horisaka ............ G01N 27/4075
                                                            204/424
2017/0045471 A1     2/2017 Maeda et al.

FOREIGN PATENT DOCUMENTS

| JP | 3756123 B2 | 3/2006 |
| JP | 3771569 B2 | 4/2006 |
| JP | 3798412 B2 | 7/2006 |
| JP | 2015-215334 A | 12/2015 |
| JP | 2016-014597 A | 1/2016 |

* cited by examiner

Primary Examiner — J. Christopher Ball
(74) Attorney, Agent, or Firm — Mattingly & Malur, PC

(57) ABSTRACT

Provided is a gas sensor having simpler configuration than a conventional multi-gas sensor, and being capable of measuring NOx and $NH_3$ simultaneously. In the gas sensor determining a NOx concentration in a measurement gas based on a pump current flowing between a NOx measurement electrode and an outer pump electrode, the outer pump electrode has catalytic activity inactivated for $NH_3$ so that a sensor element further includes a $NH_3$ sensor part having a mixed potential cell constituted by the outer pump electrode, a reference electrode, and a solid electrolyte between these electrodes, and determination of a $NH_3$ concentration based on a potential difference occurring between the outer pump electrode and the reference electrode and determination of a NOx concentration based on the pump current and the $NH_3$ concentration can be performed simultaneously or selectively when the sensor element is heated to 400° C. or higher and 600° C. or lower.

12 Claims, 6 Drawing Sheets

F I G . 3
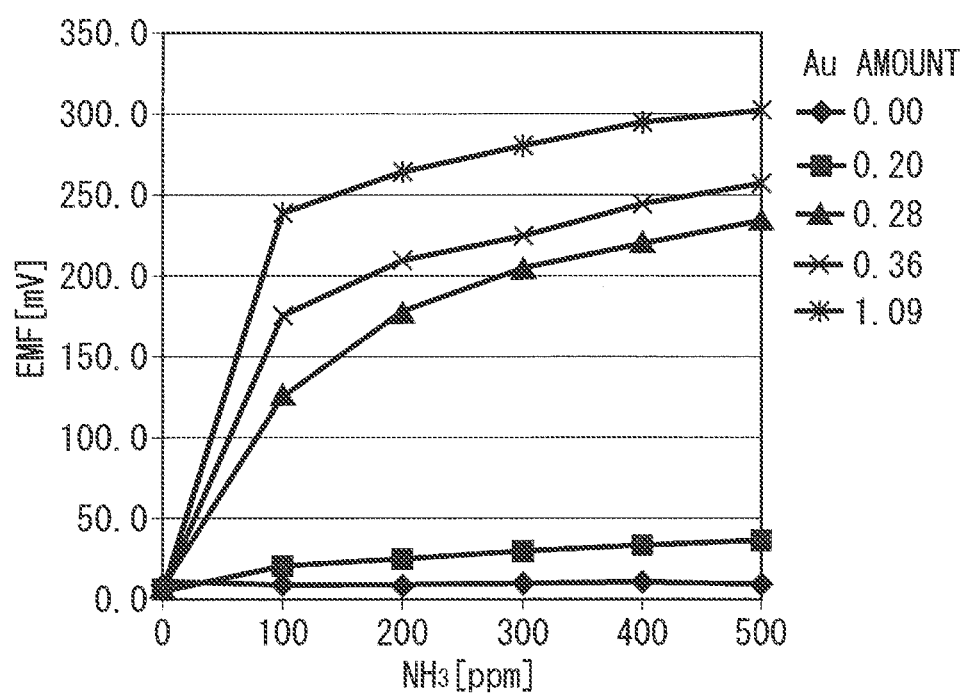

F I G . 4
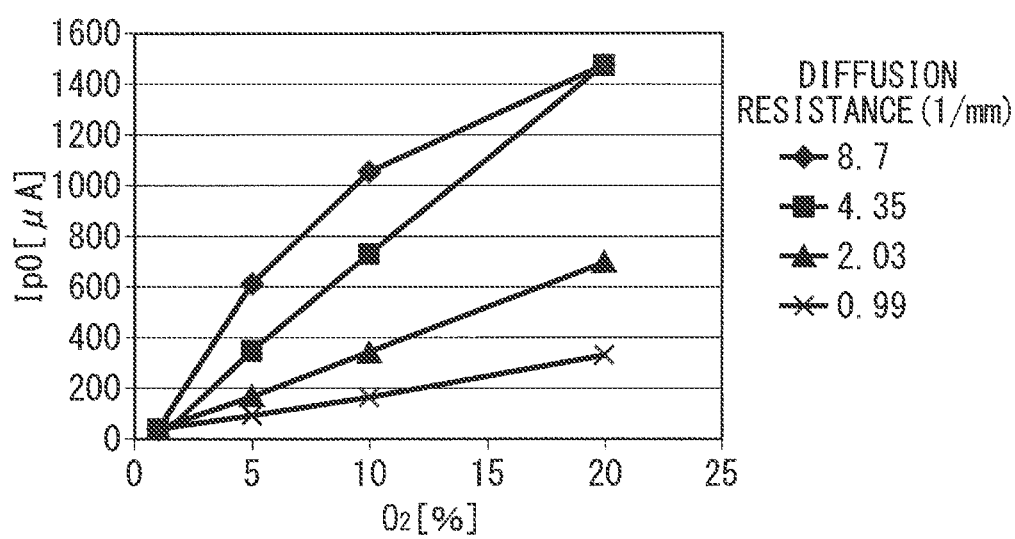

GAS SENSOR

BACKGROUND OF THE INVENTION

Field of the Invention

The present invention relates to a gas sensor for detecting a predetermined gas component in a measurement gas, and, in particular, to the configuration and the operation thereof.

Description of the Background Art

Various gas sensors have been used to obtain the concentration of a desired gas component in a measurement gas typified by an exhaust gas from an internal combustion engine, such as an engine of an automobile. For example, as an apparatus for measuring a NOx concentration in a measurement gas, such as a combustion gas, a NOx sensor including a sensor element formed of an oxygen-ion conductive solid electrolyte, such as zirconia ($ZrO_2$), is known (see, for example, Japanese Patent No. 3756123, Japanese Patent No. 3798412, and Japanese Patent No. 3771569).

A gas sensor (gas concentration measurement system) addressing the problem of ammonia ($NH_3$) interference that an output value from a NOx sensor varies depending on ammonia ($NH_3$) when ammonia ($NH_3$) exists in the measurement gas in addition to NOx is also already known (see, for example, Japanese Patent Application Laid-Open Publication No. 2015-215334 and Japanese Patent Application Laid-Open Publication No. 2016-14597).

Japanese Patent Application Laid-Open Publication No. 2015-215334 describes that an original NOx concentration can be obtained by subtracting, from a sum concentration of the original NOx concentration and the NOx concentration derived from $NH_3$ measured by a NOx sensor, the NOx concentration derived from $NH_3$ calculated based on an air fuel ratio (A/F) and a $NH_3$ concentration outside the sensor based on a certain relationship between the air fuel ratio (A/F) and a $O_2$ concentration and between the air fuel ratio (A/F) and a $H_2O$ concentration. That is to say, it is described that the $NH_3$ interference of the NOx sensor can be eliminated. In an actual automobile, however, there is no correlation between the air fuel ratio (A/F) and the $H_2O$ concentration due to condensation of water in an exhaust pipe from the engine (especially, in a cold state), EGR control, and the like. This means that it is difficult to estimate the $NH_3$ concentration outside the sensor.

Japanese Patent Application Laid-Open Publication No. 2016-14597 discloses how to calculate the $NH_3$ concentration based on two NOx concentrations obtained by changing the control temperature for the NOx sensor. A zirconia electrolyte included in the sensor element, however, has a higher resistance and passes less current therethrough at a lower temperature, and thus pumping of $O_2$ and reduction of NOx are less likely to be suitably performed when the control temperature for the NOx sensor is low. It is also assumed that switching has to be performed at long intervals due to the need to wait for stabilization of the temperature of the sensor element each time the control temperature is switched. It is thus expected to be difficult to measure the concentration in real time during actual operation of an internal combustion engine using the gas concentration measurement system disclosed in Japanese Patent Application Laid-Open Publication No. 2016-14597.

SUMMARY

The present invention relates to a gas sensor for detecting a predetermined gas component in a measurement gas, and is directed, in particular, to the configuration and the operation thereof.

According to the present invention, a gas sensor for detecting a predetermined gas component in a measurement gas includes: a sensor element including a lamination of a plurality of oxygen-ion conductive solid electrolyte layers; and a heater located inside the sensor element to heat the sensor element. The sensor element includes: a NOx sensor part; and a $NH_3$ sensor part. The NOx sensor part includes: a gas inlet through which the measurement gas is introduced from an external space; at least one internal space into which the measurement gas is introduced; a front-end diffusion resistance providing part located between the external space and the at least one internal space to provide a diffusion resistance of 0.90 (1/mm) or higher and 6.00 (1/mm) or lower to the measurement gas; a NOx measurement electrode formed to face the at least one internal space; an outer pump electrode formed on a surface of the sensor element; and a reference electrode located between two of the plurality of oxygen-ion conductive solid electrolyte layers to be in contact with a reference gas, and has a measurement pump cell that is an electrochemical pump cell constituted by the NOx measurement electrode, the outer pump electrode, and a solid electrolyte between the NOx measurement electrode and the outer pump electrode. The $NH_3$ sensor part has a mixed potential cell constituted by the outer pump electrode, the reference electrode, and a solid electrolyte between the outer pump electrode and the reference electrode, the outer pump electrode having catalytic activity inactivated for $NH_3$. The gas sensor is configured to be, in a state in which the heater heats the sensor element to an element control temperature of 400° C. or higher and 600° C. or lower, capable of simultaneously in parallel or selectively performing: determination of a $NH_3$ concentration based on a potential difference occurring between the outer pump electrode and the reference electrode in the mixed potential cell; and determination of a NOx concentration in the measurement gas based on the $NH_3$ concentration and a pump current flowing between the NOx measurement electrode and the outer pump electrode in a state of controlling a voltage applied across the NOx measurement electrode and the outer pump electrode to maintain a potential difference between the NOx measurement electrode and the reference electrode constant.

According to the present invention, a gas sensor (multi-gas sensor) capable of simultaneously or selectively performing determination of the $NH_3$ concentration and determination of the NOx concentration in the measurement gas without changing the element control temperature is achieved without complicating the configuration of a conventional NOx sensor.

Measurement of the potential difference for determination of the $NH_3$ concentration and measurement of the pump current for determination of the NOx concentration are preferably performed while being switched at time intervals of 100 msec or shorter, and the measurement pump cell is preferably suspended during measurement of the potential difference.

Alternatively, measurement of the potential difference for determination of the $NH_3$ concentration and measurement of the pump current for determination of the NOx concentration are preferably capable of being selectively performed at any timing, and the measurement pump cell is preferably suspended during measurement of the potential difference.

In either case, the $NH_3$ concentration can be obtained with higher precision compared with a case where the $NH_3$ concentration and the NOx concentration are determined simultaneously.

An object of the present invention is thus to provide a gas sensor capable of simultaneously measuring the NOx concentration and the $NH_3$ concentration at one control temperature, and also capable of performing measurement of the NOx concentration and measurement of the $NH_3$ concentration while switching therebetween.

These and other objects, features, aspects and advantages of the present invention will become more apparent from the following detailed description of the present invention when taken in conjunction with the accompanying drawings.

BRIEF DESCRIPTION OF THE DRAWINGS

FIG. 3 shows the relationship between electromotive force EMF occurring in a mixed potential cell 61 and a $NH_3$ concentration;

FIG. 4 shows $O_2$ pumping ability in a main pump cell 21 for a plurality of gas sensors 100 having different front-end diffusion resistances;

DESCRIPTION OF THE PREFERRED EMBODIMENTS

Schematic Configuration of Gas Sensor

Figure 1:
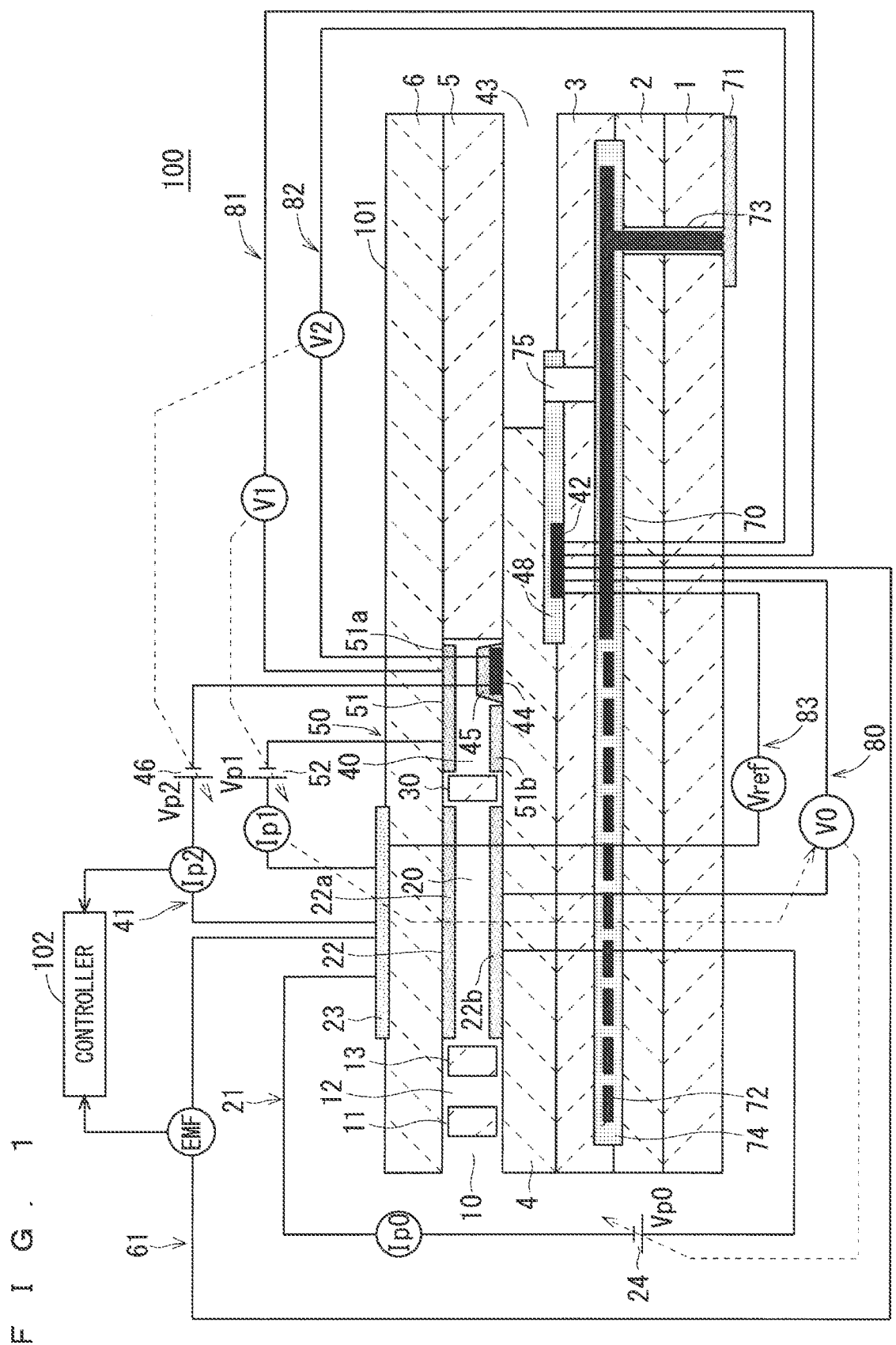
FIG. 1 schematically shows an example of the configuration of a gas sensor 100 including a vertical sectional view taken along the longitudinal direction of a sensor element 101.

Schematic configuration of a gas sensor 100 according to the present embodiment will be described. FIG. 1 schematically shows an example of the configuration of the gas sensor 100 including a vertical sectional view taken along the longitudinal direction of a sensor element 101, which is a main component of the gas sensor 100. The sensor element 101 has a structure in which six layers, namely, a first substrate layer 1, a second substrate layer 2, a third substrate layer 3, a first solid electrolyte layer 4, a spacer layer 5, and a second solid electrolyte layer 6, each being an oxygen-ion conductive solid electrolyte layer formed, for example, of zirconia ($ZrO_2$), are laminated in the stated order from the bottom side of FIG. 1. Solid electrolytes forming these six layers are dense and airtight. The sensor element 101 is manufactured, for example, by performing predetermined machining and printing of circuit patterns with respect to ceramic green sheets corresponding to respective layers, then laminating these green sheets, and further firing the laminated green sheets for integration.

Between a lower surface of the second solid electrolyte layer 6 and an upper surface of the first solid electrolyte layer 4 at one end portion of the sensor element 101, a gas inlet 10, a first diffusion control part 11, a buffer space 12, a second diffusion control part 13, a first internal space 20, a third diffusion control part 30, and a second internal space 40 are formed adjacent to each other to communicate in the stated order.

The gas inlet 10, the buffer space 12, the first internal space 20, and the second internal space 40 are spaces inside the sensor element 101 that look as if they were provided by hollowing out the spacer layer 5, and that have an upper portion, a lower portion, and a side portion respectively defined by the lower surface of the second solid electrolyte layer 6, the upper surface of the first solid electrolyte layer 4, and a side surface of the spacer layer 5.

The first diffusion control part 11, the second diffusion control part 13, and the third diffusion control part 30 are each provided as two horizontally long slits (openings whose longitudinal direction is a direction perpendicular to the plane of FIG. 1). A part extending from the gas inlet 10 to the second internal space 40 is also referred to as a gas distribution part.

At a location farther from the end portion than the gas distribution part is, a reference gas introduction space 43 having a side portion defined by a side surface of the first solid electrolyte layer 4 is provided between an upper surface of the third substrate layer 3 and a lower surface of the spacer layer 5. Atmospheric air is introduced as a reference gas into the reference gas introduction space 43.

An atmospheric air introduction layer 48 is a layer formed of porous alumina, and the atmospheric air as the reference gas is introduced into the atmospheric air introduction layer 48 through the reference gas introduction space 43. The atmospheric air introduction layer 48 is formed to cover a reference electrode 42.

The reference electrode 42 is an electrode formed to be sandwiched between the upper surface of the third substrate layer 3 and the first solid electrolyte layer 4, and the atmospheric air introduction layer 48 leading to the reference gas introduction space 43 is provided around the reference electrode 42, as described above. As will be described below, an oxygen concentration (oxygen partial pressure) in the first internal space 20 and the second internal space 40 can be measured using the reference electrode 42.

In the gas distribution part, the gas inlet 10 opens to an external space, and a measurement gas is taken from the external space into the sensor element 101 through the gas inlet 10.

The first diffusion control part 11 is a part providing a predetermined diffusion resistance to the measurement gas taken through the gas inlet 10.

The buffer space 12 is a space provided to guide the measurement gas introduced from the first diffusion control part 11 to the second diffusion control part 13.

The second diffusion control part 13 is a part providing a predetermined diffusion resistance to the measurement gas introduced from the buffer space 12 into the first internal space 20.

When the measurement gas is introduced from the outside of the sensor element 101 into the first internal space 20, the measurement gas, which is abruptly taken into the sensor element 101 through the gas inlet 10 due to pressure fluctuation of the measurement gas in the external space (pulsation of exhaust pressure in a case where the measurement gas is an exhaust gas of an automobile), is not directly introduced into the first internal space 20, but is introduced into the first internal space 20 after the concentration fluctuation of the measurement gas is canceled through the first diffusion control part 11, the buffer space 12, and the second diffusion control part 13. This makes the concentration fluctuation of the measurement gas introduced into the first internal space 20 almost negligible.

The first internal space 20 is provided as a space used to adjust oxygen partial pressure in the measurement gas introduced through the second diffusion control part 13. The oxygen partial pressure is adjusted by operation of a main pump cell 21.

The main pump cell 21 is an electrochemical pump cell constituted by an inner pump electrode 22, an outer pump electrode 23, and the second solid electrolyte layer 6 sandwiched between the inner pump electrode 22 and the outer pump electrode 23. The inner pump electrode 22 has a ceiling electrode portion 22a that is provided substantially on the entire lower surface of a portion of the second solid electrolyte layer 6 facing the first internal space 20. The outer pump electrode 23 is provided in a region, on an upper surface of the second solid electrolyte layer 6, corresponding to the ceiling electrode portion 22a so as to be exposed to the external space.

The inner pump electrode 22 is formed over upper and lower solid electrolyte layers (the second solid electrolyte layer 6 and the first solid electrolyte layer 4) that define the first internal space 20, and the spacer layer 5 that provides a side wall to the first internal space 20. Specifically, the ceiling electrode portion 22a is formed on the lower surface of the second solid electrolyte layer 6, which provides a ceiling surface to the first internal space 20, a bottom electrode portion 22b is formed on the upper surface of the first solid electrolyte layer 4, which provides a bottom surface to the first internal space 20, and a side electrode portion (not illustrated) is formed on a side wall surface (internal surface) of the spacer layer 5 that forms opposite side wall portions of the first internal space 20 to connect the ceiling electrode portion 22a and the bottom electrode portion 22b. The inner pump electrode 22 is thus provided in the form of a tunnel at a location where the side electrode portion is provided.

The inner pump electrode 22 is formed as a porous cermet electrode (e.g., a cermet electrode formed of $ZrO_2$ and Pt that contains Au of 1%). The inner pump electrode 22 to be in contact with the measurement gas is formed using a material having a weakened reducing ability with respect to a NOx component in the measurement gas.

Similarly, the outer pump electrode 23 is formed as a porous cermet electrode made of Pt containing a predetermined ratio of Au, namely, a Pt—Au alloy, and zirconia. The outer pump electrode 23 is formed to have catalytic activity inactivated for an ammonia ($NH_3$) gas, that is, to prevent or reduce the decomposition reaction of the $NH_3$ gas, in a predetermined concentration range. Thus, in the gas sensor 100, the potential of the outer pump electrode 23 selectively varies with respect to (has correlation with) $NH_3$ in the predetermined concentration range in accordance with the concentration thereof. In other words, the outer pump electrode 23 is provided so as to have high concentration dependence of the potential for the $NH_3$ gas in the predetermined concentration range while having low concentration dependence of the potential for other components of the measurement gas. Details of this point will be described below.

The main pump cell 21 can pump out oxygen in the first internal space 20 to the external space or pump in oxygen in the external space to the first internal space 20 by applying, using a variable power supply 24, a desired pump voltage Vp0 across the inner pump electrode 22 and the outer pump electrode 23 to allow a pump current Ip0 to flow between the inner pump electrode 22 and the outer pump electrode 23 in a positive or negative direction.

To detect an oxygen concentration (oxygen partial pressure) in the atmosphere existing in the first internal space 20, the inner pump electrode 22, the second solid electrolyte layer 6, the spacer layer 5, the first solid electrolyte layer 4, the third substrate layer 3, and the reference electrode 42 constitute an electrochemical sensor cell, namely, a main-pump-control oxygen-partial-pressure detection sensor cell 80.

The oxygen concentration (oxygen partial pressure) in the first internal space 20 can be obtained by measuring electromotive force V0 in the main-pump-control oxygen-partial-pressure detection sensor cell 80.

Furthermore, the pump current Ip0 is controlled by performing feedback control of the voltage Vp0 so that the electromotive force V0 is maintained constant. The oxygen concentration in the first internal space 20 is thereby maintained to have a predetermined constant value.

The third diffusion control part 30 is a part providing a predetermined diffusion resistance to the measurement gas having an oxygen concentration (oxygen partial pressure) controlled by the operation of the main pump cell 21 in the first internal space 20, and guiding the measurement gas to the second internal space 40.

The second internal space 40 is provided as a space to perform processing concerning determination of a nitrogen oxide (NOx) concentration in the measurement gas introduced through the third diffusion control part 30. The NOx concentration is determined, mainly in the second internal space 40 in which an oxygen concentration has been adjusted by an auxiliary pump cell 50, by the operation of a measurement pump cell 41.

After the oxygen concentration (oxygen partial pressure) is adjusted in advance in the first internal space 20, the auxiliary pump cell 50 further adjusts the oxygen partial pressure of the measurement gas introduced through the third diffusion control part in the second internal space 40. Owing to such adjustment, the oxygen concentration in the second internal space 40 can be maintained constant with high precision, and thus the gas sensor 100 is enabled to determine the NOx concentration with high precision.

The auxiliary pump cell 50 is an auxiliary electrochemical pump cell constituted by an auxiliary pump electrode 51, the outer pump electrode 23 (not limited to the outer pump electrode 23 but may be any appropriate electrode outside the sensor element 101), and the second solid electrolyte layer 6. The auxiliary pump electrode 51 has a ceiling electrode portion 51a that is provided substantially on the entire lower surface of a portion of the second solid electrolyte layer 6 facing the second internal space 40.

The auxiliary pump electrode 51 is provided in the second internal space 40 in the form of a tunnel, as with the inner pump electrode 22 provided in the first internal space 20 described previously. That is to say, the ceiling electrode portion 51a is formed on the second solid electrolyte layer 6, which provides a ceiling surface to the second internal space 40, a bottom electrode portion 51b is formed on the first solid electrolyte layer 4, which provides a bottom surface to the second internal space 40, and a side electrode portion (not illustrated) that connects the ceiling electrode portion 51a and the bottom electrode portion 51b is formed on opposite wall surfaces of the spacer layer 5, which provides a side wall to the second internal space 40. The auxiliary pump electrode 51 is thus provided in the form of a tunnel.

As with the inner pump electrode 22, the auxiliary pump electrode 51 is formed using a material having a weakened reducing ability with respect to a NOx component in the measurement gas.

The auxiliary pump cell 50 can pump out oxygen in the atmosphere existing in the second internal space 40 to the external space or pump in oxygen existing in the external space to the second internal space 40 by applying a desired voltage Vp1 across the auxiliary pump electrode 51 and the outer pump electrode 23.

In order to control the oxygen partial pressure in the atmosphere in the second internal space 40, the auxiliary pump electrode 51, the reference electrode 42, the second solid electrolyte layer 6, the spacer layer 5, the first solid electrolyte layer 4, and the third substrate layer 3 constitute an electrochemical sensor cell, namely, an auxiliary-pump-control oxygen-partial-pressure detection sensor cell 81.

The auxiliary pump cell 50 performs pumping using a variable power supply 52 whose voltage is controlled based on electromotive force V1 detected by the auxiliary-pump-control oxygen-partial-pressure detection sensor cell 81. The oxygen partial pressure in the atmosphere in the second internal space 40 is thereby controlled to a low partial pressure having substantially no effect on detection of NOx.

At the same time, a resulting pump current Ip1 is used to control electromotive force in the main-pump-control oxygen-partial-pressure detection sensor cell 80. Specifically, the pump current Ip1 is input, as a control signal, into the main-pump-control oxygen-partial-pressure detection sensor cell 80, and, through control of the electromotive force V0 thereof, the oxygen partial pressure in the measurement gas introduced through the third diffusion control part 30 into the second internal space 40 is controlled to have a gradient that is always constant. In use as a NOx sensor, the oxygen concentration in the second internal space 40 is maintained to have a constant value of approximately 0.001 ppm by the action of the main pump cell 21 and the auxiliary pump cell 50.

The measurement pump cell 41 detects NOx in the measurement gas in the second internal space 40. The measurement pump cell 41 is an electrochemical pump cell constituted by a NOx measurement electrode (hereinafter, simply referred to as a measurement electrode) 44, the outer pump electrode 23, the second solid electrolyte layer 6, the spacer layer 5, and the first solid electrolyte layer 4. The measurement electrode 44 is provided on an upper surface of a portion of the first solid electrolyte layer 4 facing the second internal space 40 to be separated from the third diffusion control part 30.

The measurement electrode 44 is a porous cermet electrode. The measurement electrode 44 also functions as a NOx reduction catalyst that reduces NOx existing in the atmosphere in the second internal space 40. The measurement electrode 44 is covered with a fourth diffusion control part 45.

The fourth diffusion control part 45 is a film formed of a porous body containing alumina ($Al_2O_3$) as a main component. The fourth diffusion control part 45 plays a role in limiting the amount of NOx flowing into the measurement electrode 44, and also functions as a protective film (measurement electrode protective layer) of the measurement electrode 44.

The measurement pump cell 41 can pump out oxygen generated through decomposition of nitrogen oxides in the atmosphere around the measurement electrode 44, and detect the amount of generated oxygen as a pump current Ip2.

In order to detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute an electrochemical sensor cell, namely, a measurement-pump-control oxygen-partial-pressure detection sensor cell 82. A variable power supply 46 is controlled based on electromotive force V2 detected by the measurement-pump-control oxygen-partial-pressure detection sensor cell 82.

The measurement gas introduced into the second internal space 40 reaches the measurement electrode 44 through the fourth diffusion control part 45 under a condition in which the oxygen partial pressure is controlled. Nitrogen oxides in the measurement gas around the measurement electrode 44 are reduced ($2NO \rightarrow N_2+O_2$) to generate oxygen. The generated oxygen is pumped by the measurement pump cell 41, and, at that time, a voltage Vp2 of the variable power supply 46 is controlled so that a control voltage V2 detected by the measurement-pump-control oxygen-partial-pressure detection sensor cell 82 is kept constant. The amount of oxygen generated around the measurement electrode 44 is proportional to a nitrogen oxide concentration in the measurement gas, and thus the NOx concentration in the measurement gas can be calculated using the pump current Ip2 in the measurement pump cell 41. When NOx and $NH_3$ coexist in the measurement gas, the value of the pump current Ip2 is affected by a $NH_3$ concentration (subject to $NH_3$ interference), and thus it is required to determine the NOx concentration in view of the $NH_3$ interference. This point will be described below.

If the measurement electrode 44, the first solid electrolyte layer 4, the third substrate layer 3, and the reference electrode 42 are combined to constitute an oxygen partial pressure detection means as an electrochemical sensor cell, electromotive force in accordance with a difference between the amount of oxygen generated through reduction of a NOx component in the atmosphere around the measurement electrode 44 and the amount of oxygen contained in reference atmospheric air can be detected, and the NOx concentration in the measurement gas can thereby be obtained.

The second solid electrolyte layer 6, the spacer layer 5, the first solid electrolyte layer 4, the third substrate layer 3, the outer pump electrode 23, and the reference electrode 42 constitute an electrochemical sensor cell 83, and oxygen partial pressure in the measurement gas outside the sensor can be detected using electromotive force Vref obtained by the sensor cell 83.

A portion of the sensor element 101 extending from the gas inlet 10 to the second internal space 40 in the longitudinal direction of the element, and further, the electrodes, the pump cells, the sensor cells, and the like provided in the portion, which are described above, relate mainly to measurement of the NOx concentration based on a limiting current scheme, and thus they are collectively referred to as a NOx sensor part of the sensor element 101 in the present embodiment.

On the other hand, in the sensor element 101, the outer pump electrode 23 is formed to have catalytic activity inactivated for the $NH_3$ gas as described above. The reference electrode 42 is located in atmospheric air (oxygen) in use of the gas sensor 100 to always have a constant potential. In the sensor element 101, the outer pump electrode 23, the reference electrode 42, and the solid electrolyte layer between the outer pump electrode 23 and the reference electrode 42 constitute a mixed potential cell 61. This means that, in the gas sensor 100, the $NH_3$ concentration in the measurement gas can also be obtained using a potential difference occurring due to the difference in $NH_3$ concentration around the outer pump electrode 23 and around the reference electrode 42 based on the principle of mixed potential.

In the present embodiment, portions of the sensor element 101 constituting the mixed potential cell 61 are collectively referred to as a $NH_3$ sensor part. The reference electrode 42 is used not only by the $NH_3$ sensor part but also by the NOx sensor part as described above, and is thus also referred to as a common reference electrode. Since the NOx sensor part and the $NH_3$ sensor part share the reference electrode 42, simplified internal configuration of the sensor element 101 and space-saving are achieved compared with a conventional multi-gas sensor in which these sensor parts have respective reference electrodes.

More specifically, in the sensor element 101, with an Au abundance ratio of the surfaces of Pt—Au alloy particles included in the outer pump electrode 23 being suitably set, the catalytic activity of the outer pump electrode 23 against a $NH_3$ gas is inactivated. Specifically, when the Au abundance ratio of the outer pump electrode 23 is 0.25 or more and 2.30 or less, the potential of the outer pump electrode 23 exhibits noticeable dependence of the potential difference (electromotive force) EMF occurring between the outer pump electrode 23 and the reference electrode 42 on the $NH_3$ concentration in a concentration range of 0 ppm to 1,000 ppm. The outer pump electrode 23 having an Au abundance ratio more than 2.30 is undesirable because oxygen pumping ability of such an outer pump electrode 23 is low.

In this specification, the Au abundance ratio means an area ratio of a portion covered with Au to a portion at which Pt is exposed in the surface of noble metal particles included in the outer pump electrode 23. In this specification, the Au abundance ratio is calculated from an expression shown below using Au and Pt detection values in an Auger spectrum obtained by performing Auger electron spectroscopy (AES) analysis on the surface of the noble metal particles.

$$\text{Au abundance ratio} = \text{Au detection value} / \text{Pt detection value} \quad (1)$$

The Au abundance ratio is one when the area of the portion at which Pt is exposed and the area of the portion covered with Au are equal to each other.

The Au abundance ratio can also be calculated using a relative sensitivity coefficient method from a peak intensity of a peak detected for Au and Pt obtained by subjecting the surface of the noble metal particles to X-ray photoelectron spectroscopy (XPS) analysis. The value of the Au abundance ratio obtained by this method can be considered to be substantially the same as the value of the Au abundance ratio calculated based on the result of AES analysis.

The Au abundance ratio expressed by the expression (1) can be considered for an electrode other than the outer pump electrode 23. In particular, the inner pump electrode 22 and the auxiliary pump electrode 51 are preferably provided to have an Au abundance ratio of 0.01 or more and 0.3 or less. In this case, the catalytic activity of the inner pump electrode 22 and the auxiliary pump electrode 51 is reduced for a substance other than oxygen to increase selective decomposing ability for oxygen. The Au abundance ratio is more preferably 0.1 or more and 0.25 or less, and is much more preferably 0.2 or more and 0.25 or less.

The sensor element 101 further includes a heater part 70 playing a role in temperature adjustment of heating the sensor element 101 and keeping it warm. The heater part 70 includes a heater electrode 71, a heater 72, a through hole 73, a heater insulating layer 74, and a pressure diffusion hole 75. The heater electrode 71 is an electrode formed to be in contact with a lower surface of the first substrate layer 1. The heater electrode 71 is to be connected to an external power supply to enable the heater part 70 to be externally powered.

The heater 72 is an electric resistor formed to be vertically sandwiched between the second substrate layer 2 and the third substrate layer 3. The heater 72 is connected to the heater electrode 71 via the through hole 73, and generates heat by being externally powered through the heater electrode 71 to heat the solid electrolytes forming the sensor element 101 and keep it warm.

The heater 72 is buried across the entire region extending from the first internal space 20 to the second internal space 40, and can thereby adjust the temperature of the sensor element 101 as a whole.

The heater insulating layer 74 is an insulating layer formed of an insulator, such as alumina, on upper and lower surfaces of the heater 72. The heater insulating layer 74 is formed for electrical insulation between the second substrate layer 2 and the heater 72 and for electrical insulation between the third substrate layer 3 and the heater 72.

The pressure diffusion hole 75 is a part provided to penetrate the third substrate layer 3 to communicate with the reference gas introduction space 43, and is formed to mitigate an internal pressure rise associated with a temperature rise in the heater insulating layer 74.

Operation of each part of the gas sensor 100, for example, application of voltages to the pump cells performed by the variable power supplies and heating performed by the heater 72, is controlled by a controller (controlling means) 102 electrically connected to each part. In addition, the controller 102 determines the NOx concentration in the measurement gas based on the pump current Ip2 flowing through the measurement pump cell 41. The controller 102 determines the $NH_3$ concentration in the measurement gas based on the electromotive force EMF occurring in the mixed potential cell 61 of the sensor element 101. This means that the controller 102 functions as a concentration determination means for determining the NOx concentration and further determining the $NH_3$ concentration. Although only a symbol of the electromotive force EMF and a symbol of the pump current Ip2 are connected to the controller 102 by arrows in FIG. 1 for clarity of illustration, it is needless to say that other values of the potential difference and values of the pump current are also provided to the controller 102. A general-purpose personal computer is applicable to the controller 102.

The sensor element 101 may include a surface protective layer (not illustrated) located on the upper surface of the second solid electrolyte layer 6 to cover the outer pump electrode 23. The surface protective layer is provided for prevention of adhesion of a poisoning substance contained in the measurement gas to the outer pump electrode 23. The surface protective layer is preferably formed of porous alumina, for example. The surface protective layer is provided to have a pore diameter and a pore size not controlling gas distribution between the outer pump electrode 23 and the outside of the element.

Process of Manufacturing Sensor Element

The process of manufacturing the sensor element 101 illustrated in FIG. 1 will be described next. Generally speaking, the sensor element 101 illustrated in FIG. 1 is manufactured by forming a laminated body formed of green sheets containing an oxygen-ion conductive solid electrolyte, such as zirconia, as a ceramic component, and by cutting and firing the laminated body. The oxygen-ion conductive solid electrolyte is, for example, yttrium partially stabilized zirconia (YSZ) obtained by internally adding, to zirconia, yttria at a proportion of 3 mol % or more.

Figure 2:
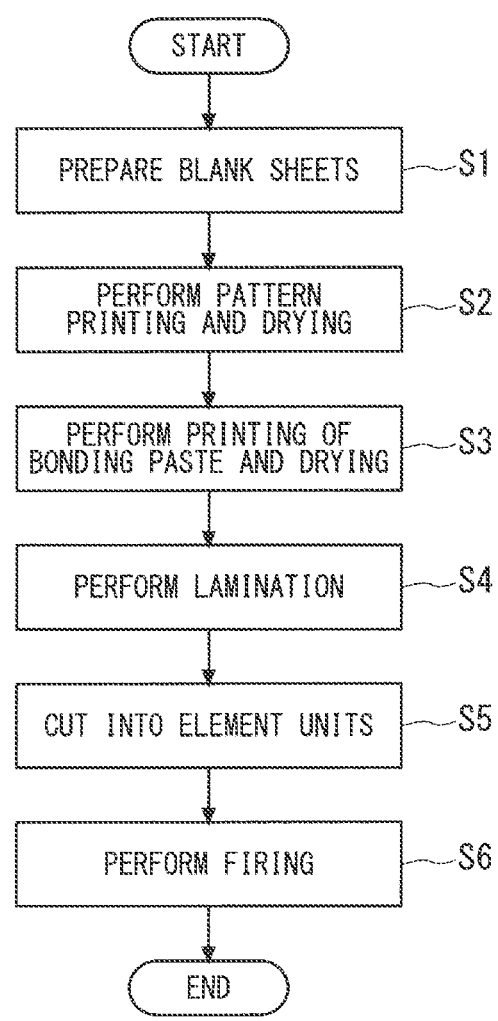
FIG. 2 shows a processing flow in the manufacture of the sensor element 101.

FIG. 2 shows a processing flow in the manufacture of the sensor element 101. In the manufacture of the sensor element 101, blank sheets (not illustrated) that are green sheets having no pattern formed thereon are prepared first (step S1). Specifically, six blank sheets corresponding to the first substrate layer 1, the second substrate layer 2, the third substrate layer 3, the first solid electrolyte layer 4, the spacer layer 5, and the second solid electrolyte layer 6 are prepared. The blank sheets have a plurality of sheet holes used for positioning in printing and lamination. The sheet holes are formed in advance through, for example, punching by a punching machine. Green sheets corresponding to layers forming an internal space also include penetrating portions corresponding to the internal space formed in advance through, for example, punching as described above. The blank sheets corresponding to the respective layers of the sensor element 101 are not required to have the same thickness.

After preparation of the blank sheets corresponding to the respective layers, pattern printing and drying are performed to form various patterns on the individual blank sheets (step S2). Specifically, the electrode pattern of each pump electrode, the pattern of the heater 72, the atmospheric air introduction layer 48, internal wiring (not illustrated), and the like are formed. The pattern of the surface protective layer may further be printed. With respect to the first substrate layer 1, a cut mark serving as a reference cut position when the laminated body is cut in a subsequent step is printed.

Each pattern is printed by applying, to the blank sheet, a paste for pattern formation prepared in accordance with the characteristics required for each formation target using a known screen printing technique. Any known drying means is available for drying after printing.

After pattern printing, printing of a bonding paste and drying are performed to laminate and bond the green sheets corresponding to the respective layers (step S3). Any known screen printing technique is available for printing of the bonding paste, and any known drying means is available for drying after printing.

Then, the green sheets to which an adhesive has been applied are stacked in a predetermined order, and the stacked green sheets are crimped under predetermined temperature and pressure conditions to thereby form a laminated body (step S4). Specifically, crimping is performed by stacking and holding the green sheets as a target of lamination in a predetermined lamination jig (not illustrated) while positioning the green sheets at the sheet holes, and then heating and pressurizing the green sheets together with the lamination jig using a lamination machine, such as a known hydraulic pressing machine. The pressure, temperature, and time for heating and pressurizing depend on a lamination machine to be used, and these conditions may be set appropriately to achieve good lamination. The surface protective layer may be formed on the laminated body as obtained.

After the laminated body is obtained as described above, the laminated body is cut out at a plurality of positions to obtain individual units (referred to as element bodies) of the sensor element 101 (step S5). The cut out element bodies are fired under predetermined conditions, thereby producing the sensor element 101 as described above (step S6). This means that the sensor element 101 is produced by integral firing (co-firing) of the solid electrolyte layers and the electrodes. The firing temperature is preferably 1,200° C. or higher and 1,500° C. or lower (e.g., 1,400° C.). Integral firing performed in such a manner provides sufficient adhesion strength to each of the electrodes of the sensor element 101. This contributes to improvement in durability of the sensor element 101.

The sensor element 101 thus obtained is housed in a predetermined housing, and incorporated into a main body (not illustrated) of the gas sensor 100.

The paste for pattern (a conductive paste) used to form the outer pump electrode 23 by printing can be produced by using an Au ion-containing liquid as an Au starting material and mixing the Au ion-containing liquid with powdered Pt, powdered zirconia, and a binder. Any binder, which can disperse any other raw material to the printable extent and vanishes through firing, may be appropriately selected.

The Au ion-containing liquid is obtained by dissolving a salt containing an Au ion or an organometallic complex containing an Au ion in a solvent. The Au ion-containing salt may be, for example, tetrachloroauric(III) acid ($HAuCl_4$), sodium chloroaurate(III) ($NaAuCl_4$), or potassium dicyanoaurate(I) ($KAu(CN)_2$). The Au ion-containing organometallic complex may be, for example, gold(III) diethylenediamine trichloride ($[Au(en)_2]Cl_3$), gold(III) dichloro(1,10-phenanthroline)chloride ($[Au(phen)Cl_2]Cl$), dimethyl (trifluoroacetylacetonate)gold, or dimethyl (hexafluoroacetylacetonate)gold. Tetrachloroauric(III) acid or gold(III) diethylenediamine chloride ($[Au(en)_2]Cl_3$) is preferably used from the viewpoint of no impurity such as Na or K remaining in the electrode, easy handling, or dissolvability in the solvent. The solvent may be acetone, acetonitrile, or formamide as well as alcohols such as methanol, ethanol, and propanol.

Mixing can be performed by well-known means such as instillation. Although the obtained conductive paste contains Au present in ionic (complex ionic) state, the outer pump electrode 23 formed in the sensor element 101 obtained through the above-mentioned manufacturing process contain Au mainly as an elemental substrate or an alloy with Pt.

Alternatively, the conductive paste for the outer pump electrode 23 may be prepared by using coated powder, which is obtained by coating powdered Pt with Au, as a starting raw material, instead of preparing the paste through liquid-state Au mixing as described above. In such a case, a conductive paste for the outer pump electrode is prepared by mixing the coated powder, zirconia powder, and a binder. Here, the coated powder may be obtained by covering the particle surface of powdered Pt with an Au film or applying Au particles to Pt powder particles.

Simultaneous Measurement Mode

In use of the gas sensor 100 having the configuration as described above, the gas sensor 100 is located so that a predetermined range of the sensor element 101 including the gas inlet 10 at one end portion is located in the atmosphere of the measurement gas, and the other end portion is not in contact with the atmosphere of the measurement gas. The sensor element 101 is then heated by the heater 72 to a predetermined temperature (hereinafter, element control temperature) of 400° C. or higher and 600° C. or lower. This temperature range is a temperature range in which the mixed potential cell 61 suitably operates. In the present embodiment, the element control temperature is evaluated using the temperature at the location of the outer pump electrode 23. The temperature can be evaluated, for example, by infrared thermography.

That temperature range, however, is lower than a temperature range (of 600° C. or higher and 900° C. or lower) in which the solid electrolytes included in the sensor element 101 demonstrate favorable oxygen ion conductivity. Thus, by only simply setting the element control temperature as described above, the oxygen ion conductivity of the solid electrolytes included in the sensor element 101 is not sufficiently demonstrated, and each pump cell (especially, the main pump cell 21) in the NOx sensor part cannot sufficiently pump out oxygen from the internal space.

In view of this point, the sensor element 101 is configured so that each pump cell in the NOx sensor part suitably operates even at the element control temperature of 400° C. or higher and 600° C. or lower, by increasing the diffusion resistance (hereinafter, front-end diffusion resistance) provided to the measurement gas flowing through the gas inlet 10 and then reaching the first internal space 20 compared with a case where the element control temperature is 600° C. or higher and 900° C. or lower, so as to limit the amount of the measurement gas reaching the first internal space 20. This can be achieved, for example, by increasing the diffusion resistance provided by the first diffusion control part 11 and the second diffusion control part 13 to the measurement gas compared with the case where the element control temperature is 600° C. or higher and 900° C. or lower. Alternatively, a porous protective film having a predetermined pore ratio may be provided at one end portion of the sensor element 101 to at least cover the gas inlet 10. A part of the sensor element 101 located between the external space and the first internal space 20 to provide the front-end diffusion resistance is referred to as a front-end diffusion resistance providing part.

Specifically, the front-end diffusion resistance is 0.90 (1/mm) or higher and 6.00 (1/mm) or lower.

Accordingly, in the gas sensor 100, the $NH_3$ sensor part and the NOx sensor part operate concurrently by heating the sensor element 101 to the predetermined element control temperature, and generation of the pump current based on oxygen pumping in the pump cell including the outer pump electrode 23 and the occurrence of the potential difference in the mixed potential cell 61 are simultaneously achieved in parallel. This means that, despite having similar components to a conventional limiting current NOx sensor, the gas sensor 100 according to the present embodiment can measure NOx and $NH_3$ in the measurement gas simultaneously. In other words, the gas sensor 100 according to the present embodiment can measure NOx and $NH_3$ in the measurement gas simultaneously by only changing the composition of the outer pump electrode 23 and setting the front-end diffusion resistance to a value suitable for the element control temperature without providing, to the conventional NOx sensor, an additional component enabling the conventional NOx sensor to function as the $NH_3$ sensor. That is to say, in the present embodiment, the gas sensor capable of measuring NOx and $NH_3$ in the measurement gas simultaneously is achieved without complicating the configuration of the conventional NOx sensor.

In the present embodiment, a mode in which the gas sensor 100 measures NOx and $NH_3$ in the measurement gas simultaneously is referred to as a simultaneous measurement mode.

As described above, however, the value of the pump current Ip2 varies depending on the $NH_3$ concentration in the measurement gas when NOx and $NH_3$ coexist in the measurement gas. It is thus not always appropriate to obtain the NOx concentration directly from the value of the pump current Ip2 as obtained from a viewpoint of precision, and it is preferable to make a correction based on the $NH_3$ concentration.

In the present embodiment, the NOx concentration and the $NH_3$ concentration are obtained, for example, in accordance with procedures as described below using the fact that the value of the potential difference EMF obtained in the mixed potential cell 61 is not subject to interference of the NOx concentration when NOx and $NH_3$ coexist in the measurement gas. Not only the $NH_3$ concentration but also the NOx concentration can thus be obtained with high precision even when NOx and $NH_3$ coexist in the measurement gas. That is to say, the gas sensor 100 according to the present embodiment can obtain the NOx concentration and the $NH_3$ concentration in the measurement gas simultaneously with high precision.

(1) Preparing in advance a NOx concentration map indicating the relationship among the $NH_3$ concentration, the NOx concentration, and the pump current Ip2, and a $NH_3$ concentration map indicating the relationship between the potential difference EMF occurring in the mixed potential cell 61 and the $NH_3$ concentration, using a plurality of model gases of known concentrations corresponding to different combinations of the NOx concentration and the $NH_3$ concentration, and storing the NOx concentration map and the $NH_3$ concentration map in the controller 102, which is a concentration determination means.

(2) In actual use of the gas sensor 100, acquiring, at the controller 102, the value of the potential difference EMF occurring in the mixed potential cell 61 and the value of the pump current Ip2 flowing through the measurement pump cell 41 at an appropriate timing.

(3) Determining the $NH_3$ concentration by collating, at the controller 102, the value of the potential difference EMF as acquired with the $NH_3$ concentration map.

(4) Then determining the NOx concentration by collating the value of the pump current Ip2 and the $NH_3$ concentration as determined previously with the NOx concentration map.

(5) Repeating the procedures (2) to (4) in the case of continuously obtaining the NOx concentration.

As described above, in the gas sensor 100 according to the present embodiment, the measurement pump cell 41 through which the pump current Ip2 flows and the mixed potential cell 61 in which the potential difference EMF occurs share the reference electrode 42 located inside the atmospheric air introduction layer 48 and being in contact with atmospheric air always having a constant oxygen concentration. Thus, both of the oxygen pump current Ip2 and the potential difference EMF are obtained with stability. This also contributes to improvement in precision in determining the NOx concentration and the $NH_3$ concentration.

Specific Example in Case Where Element Control Temperature is Set to 600° C.

A specific example of the gas sensor 100 capable of performing the concurrent measurement mode will be described below by taking a case where the element control temperature is set to 600° C. as an example.

FIG. 3 shows the relationship between the electromotive force EMF occurring in the mixed potential cell 61 and the $NH_3$ concentration for each of the gas sensors 100 including the mixed potential cells 61 in which the outer pump electrodes 23 have different Au abundance ratios. Specifically, for each of five gas sensors 100 including the outer pump electrodes 23 having different Au abundance ratios while having the configuration shown in FIG. 1, the electromotive force EMF occurring in the mixed potential cell 61 was measured under conditions shown below using six model gases having different $NH_3$ concentrations. FIG. 3 was obtained by plotting, with respect to the $NH_3$ concentration, values of the electromotive force EMF as obtained. The Au abundance ratio of the outer pump electrode 23 was at five levels, namely, 0, 0.2, 0.28, 0.36, and 1.09. The front-end diffusion resistance was 4.35 (1/mm).

Model Gas Conditions

Flow rate: 5 L/min;
Gas temperature: 120° C.; and
Gas composition:
$O_2$=10%;
$H_2O$=5%;
$NH_3$=0 ppm, 100 ppm, 200 ppm, 300 ppm, 400 ppm, or 500 ppm; and
$N_2$=balance.

It is confirmed from FIG. 3 that, in a case where the Au abundance ratio of the outer pump electrode 23 is 0.28 to 1.09, the electromotive force EMF occurring in the mixed potential cell 61 has noticeable dependence on the $NH_3$ concentration. This means that the gas sensor 100 can measure the $NH_3$ concentration in a case where the Au abundance ratio of the outer pump electrode 23 is at least set to a value within a range of 0.28 to 1.09.

FIG. 4 shows $O_2$ pumping ability in the main pump cell 21 for each of a plurality of gas sensors 100 having different front-end diffusion resistances. Specifically, for each of four gas sensors 100 having different front-end diffusion resistances while having the configuration shown in FIG. 1, the pump current Ip0 in the main pump cell 21 was measured under conditions shown below using four model gases having different $O_2$ concentrations. FIG. 4 was obtained by plotting, with respect to the $O_2$ concentration, values of the pump current Ip0 as obtained. The front-end diffusion resistance was at four levels, namely, 0.99 (1/mm), 2.03 (1/mm), 4.35 (1/mm), and 8.7 (1/mm). The Au abundance ratio of the outer pump electrode 23 was 1.09. Furthermore, when the NOx sensor part operated, feedback control was performed on the variable power supplies 24, 52, and 46 respectively corresponding to the main-pump-control oxygen-partial-pressure detection sensor cell 80, the auxiliary-pump-control oxygen-partial-pressure detection sensor cell 81, and the measurement-pump-control oxygen-partial-pressure detection sensor cell 82 so that the electromotive forces V0, V1, and V2 in the respective sensor cells were respectively 300 mV, 380 mV, and 400 mV.

Model Gas Conditions

Flow rate: 5 L/min;
Gas temperature: 120° C.; and
Gas composition:
$O_2$=1%, 5%, 10%, or 20%;
$H_2O$=5%; and
$N_2$=balance.

It is confirmed from FIG. 4 that, in three gas sensors 100 having front-end diffusion resistances of 0.99 (1/mm) to 4.35 (1/mm), the pump current Ip0 linearly varies depending on the $O_2$ concentration. This means that, in a case where the sensor element 101 is configured so that the front-end diffusion resistance at least has a value within a range of 0.99 (1/mm) to 4.35 (1/mm), the main pump cell 21 including the outer pump electrode 23 can perform $O_2$ pumping without any problems at least in a range of the $O_2$ concentration of 20% or lower even when the element control temperature is set to 600° C.

It is needless to say that the auxiliary pump cell 50 and the measurement pump cell 41 can perform $O_2$ pumping without any problems because the main pump cell 21, which is required to pump the largest amount of $O_2$, can suitably perform pumping.

It is obvious that the outer pump electrode 23 having a smaller Au abundance ratio has higher $O_2$ pumping ability. It can thus be said that, in the gas sensors 100 having Au abundance ratios of 0.28 and 0.36, which shows favorable results in FIG. 3, $O_2$ pumping is performed without any problems.

That is to say, it can be said that, in the gas sensor 100 in which the front-end diffusion resistance is set to a value at least within a range of 0.99 (1/mm) to 4.35 (1/mm), $O_2$ pumping is performed without any problems even when the Au abundance ratio of the outer pump electrode 23 has a value within a range of 0.28 to 1.09 and when the element control temperature is set to 600° C.

On the other hand, it is confirmed that the gas sensor 100 having a front-end diffusion resistance of 8.7 (1/mm) tends to have smaller variation as the $O_2$ concentration increases. This means that pumping is not performed appropriately when the $O_2$ concentration is high. Use of the gas sensor 100 having such configuration in measurement is undesirable because the oxygen partial pressure of the measurement gas reaching the measurement electrode 44 cannot be reduced to the extent having substantially no effect on NOx detection, and, as a result, the pump current Ip2 cannot be obtained in accordance with the NOx concentration.

Figure 5A:
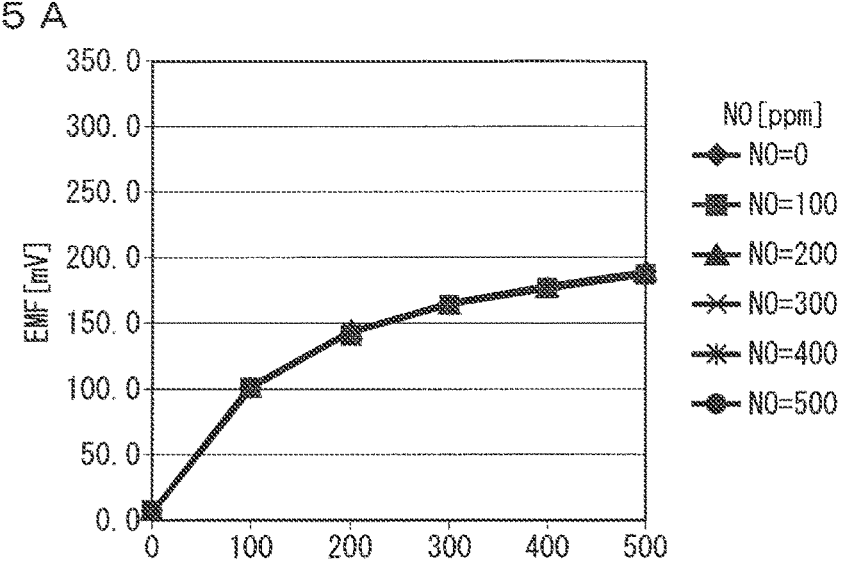
FIGS. 5A, 5B, and 5C each show, for a gas sensor 100 in which noticeable dependence of the electromotive force EMF occurring in the mixed potential cell 61 on the $NH_3$ concentration is exhibited, the dependence of the electromotive force EMF on the $NH_3$ concentration when $NH_3$ and NOx coexist in a measurement gas.
Figure 5B:
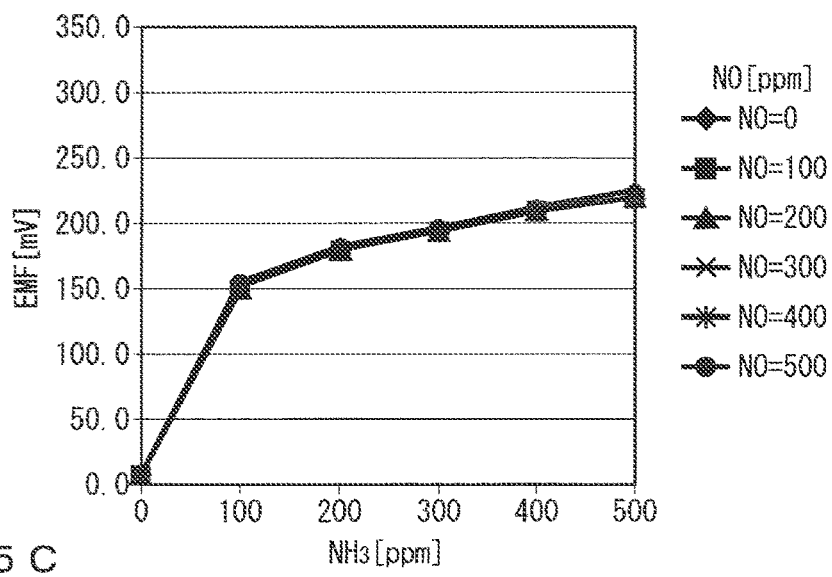
Figure 5C:
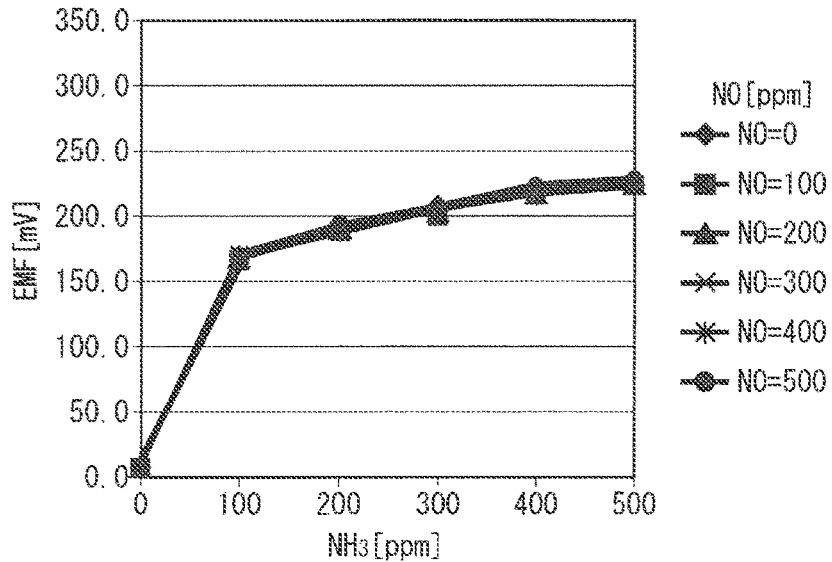

FIGS. 5A, 5B, and 5C respectively show, for three gas sensors 100 having Au abundance ratios of the outer pump electrode 23 of 0.28, 0.36, and 1.09, in which noticeable dependence of the electromotive force EMF occurring in the mixed potential cell 61 on the $NH_3$ concentration is confirmed to be exhibited from the results shown in FIG. 3, the dependence of the electromotive force EMF on the $NH_3$ concentration in the case that $NH_3$ and NOx coexist in the measurement gas. Specifically, for each of the three gas sensors 100, the electromotive force EMF occurring in the mixed potential cell 61 was measured under conditions shown below using all 36 model gases having different combinations of six levels of the $NH_3$ concentration and six levels of the NO concentration. FIGS. 5A, 5B, and 5C were obtained by plotting, with respect to the $NH_3$ concentration, values of the electromotive force EMF as obtained. FIGS. 5A, 5B, and 5C respectively show the results concerning the gas sensors 100 having Au abundance ratios of the outer pump electrodes 23 of 0.28, 0.36, and 1.09. The values of the electromotive forces V0, V1, and V2 were controlled as in a case where the results shown in FIG. 4 were obtained.

Model Gas Conditions

Flow rate: 5 L/min;
Gas temperature: 120° C.; and
Gas composition:
$O_2$=10%;
$H_2O$=5%;
$NH_3$=0 ppm, 100 ppm, 200 ppm, 300 ppm, 400 ppm, or 500 ppm;

NO=0 ppm, 100 ppm, 200 ppm, 300 ppm, 400 ppm, or 500 ppm; and

N$_2$=balance.

It is confirmed from FIGS. 5A, 5B, and 5C that, in each of the three gas sensors 100, the dependence of the potential difference EMF on the NH$_3$ concentration does not vary depending on the NO concentration. This means that the value of the potential difference EMF obtained in the mixed potential cell 61 is not subject to interference of the NOx concentration, and thus the NH$_3$ concentration in the measurement gas can be determined based on the value of the potential difference EMF obtained in the mixed potential cell 61 even when NH$_3$ and NOx coexist in the measurement gas. This also means that the results shown in FIGS. 5A, 5B, and 5C can be used as the NH$_3$ concentration map when the NOx concentration is to be obtained using each of the gas sensors 100.

The electromotive force EMF occurring in the mixed potential cell 61 has nothing to do with the value of the front-end diffusion resistance, and thus the gas sensors 100 having the same Au abundance ratio of the outer pump electrode 23 can use the results shown in FIGS. 5A, 5B, and 5C as the NH$_3$ concentration map even when the gas sensors 100 had different values of the front-end diffusion resistance.

Figure 6A:
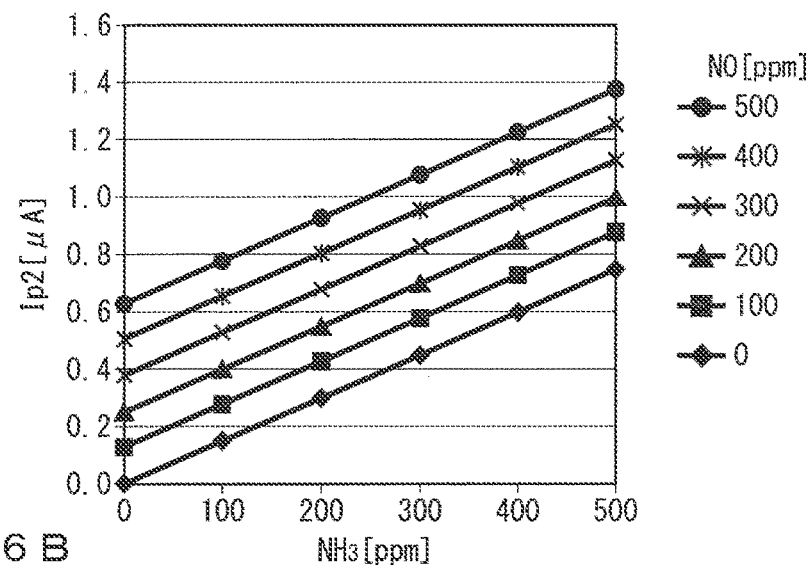
FIGS. 6A, 6B, and 6C each show, for a gas sensor 100 in which $O_2$ pumping is performed without any problems, $NH_3$ concentration dependence of a pump current Ip2 when $NH_3$ and NOx coexist in the measurement gas.
Figure 6B:
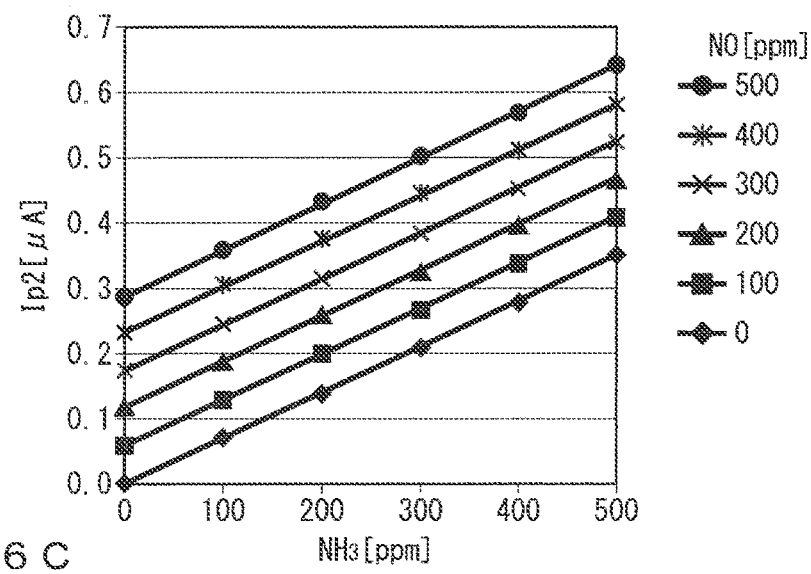
Figure 6C:
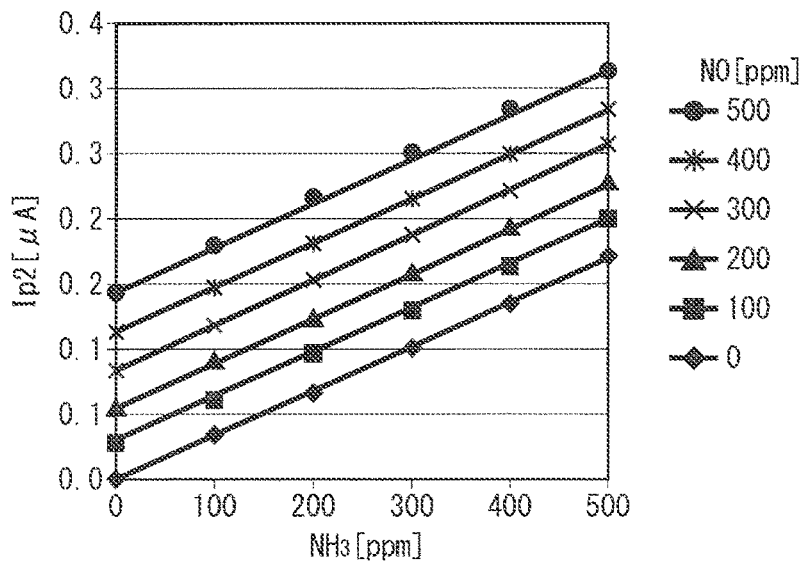

FIGS. 6A, 6B, and 6C respectively show, for three gas sensors 100 having front-end diffusion resistances of 4.35 (1/mm), 2.03 (1/mm), and 0.99 (1/mm), in which O$_2$ pumping is confirmed to be performed without any problems from the results shown in FIG. 4, the NH$_3$ concentration dependence of the pump current Ip2 in the case that NH$_3$ and NOx coexist in the measurement gas. Specifically, for each of the three gas sensors 100, the pump current Ip2 was measured under conditions shown below using all 36 model gases having different combinations of six levels of the NH$_3$ concentration and six levels of the NO concentration. FIGS. 6A, 6B, and 6C were obtained by plotting, with respect to the NH$_3$ concentration, values of the pump current Ip2 as obtained. FIGS. 6A, 6B, and 6C show the results concerning the gas sensors 100.

Model Gas Conditions

Flow rate: 5 L/min;
Gas temperature: 120° C.; and
Gas composition:
NH$_3$=0 ppm, 100 ppm, 200 ppm, 300 ppm, 400 ppm, or 500 ppm;
NO=0 ppm, 100 ppm, 200 ppm, 300 ppm, 400 ppm, or 500 ppm;
O$_2$=10%; and
N$_2$=balance.

It is confirmed from FIGS. 6A, 6B, and 6C that, in each of the three gas sensors 100, the pump current Ip2 varies depending on the NH$_3$ concentration even when the NO concentration is constant. On the other hand, it is also confirmed that, in each of the three gas sensors 100, the pump current Ip2 linearly varies depending on the NH$_3$ concentration when the NO concentration is constant. This means that the results shown in FIGS. 6A, 6B, and 6C can be used as the NOx concentration map when the NOx concentration is to be obtained using each of the gas sensors 100.

The front-end diffusion resistance has nothing to do with the mixed potential cell 61, and thus the gas sensors 100 having the same front-end diffusion resistance can use the results shown in FIGS. 6A, 6B, and 6C as the NOx concentration map even when the gas sensors 100 has different Au abundance ratios of the outer pump electrode 23.

It can thus be said that FIGS. 5A, 5B, 5C, 6A, 6B, and 6C show the NH$_3$ concentration map and the NOx concentration map for all nine gas sensors 100 having an Au abundance ratio of the outer pump electrode 23 of any of 0.28, 0.36, and 1.09 and having a front-end diffusion resistance of any of 4.35 (1/mm), 2.03 (1/mm), and 0.99 (1/mm). Thus, in a case where any of all the nine gas sensors 100 is used, the NH$_3$ concentration and the NOx concentration in the measurement gas can be obtained simultaneously with high precision in the simultaneous measurement mode by using the corresponding concentration map.

As for the gas sensor 100 in which at least one of the Au abundance ratio of the outer pump electrode 23 and the front-end diffusion resistance is different from that in the above-mentioned cases, the NH$_3$ concentration and the NOx concentration in the measurement gas can naturally be obtained simultaneously with high precision in the simultaneous measurement mode by preparing in advance the NH$_3$ concentration map as shown in FIGS. 5A, 5B, and 5C and the NOx concentration map as shown in FIGS. 6A, 6B, and 6C as long as each of the Au abundance ratio of the outer pump electrode 23 and the front-end diffusion resistance has a value in a preferable range.

Switching Measurement Mode

The gas sensor 100 according to the present embodiment can not only measure NOx and NH$_3$ in the measurement gas simultaneously in the above-mentioned simultaneous measurement mode, but also perform measurement of NOx using the NOx sensor part and measurement of NH$_3$ using the NH$_3$ sensor part while switching therebetween. Such a measurement mode is referred to as a switching measurement mode.

In the switching measurement mode, measurement of the electromotive force EMF performed by the NH$_3$ sensor part in a state of suspending control of the NOx sensor part performed by the controller 102, specifically, in a state of suspending control of oxygen pumping performed by each pump cell, acquisition of the output value including the pump current Ip2, and the like, and measurement of the pump current Ip2 performed by the NOx sensor part in a state of suspending control of the NH$_3$ sensor part performed by the controller 102, specifically, in a state of suspending acquisition of the electromotive force EMF and the like are performed while being switched at predetermined time intervals.

In this case, especially the NH$_3$ concentration can be calculated with higher precision than that in the simultaneous measurement mode. This is because, although the NH$_3$ concentration to be calculated in the simultaneous measurement mode may include a minor error caused by the fact that the electromotive force EMF is always measured in a state in which the outer pump electrode 23 performs oxygen pumping, such an error is not caused in the switching measurement mode since the pump cell does not operate during measurement of the electromotive force EMF.

The above-mentioned error caused in the simultaneous measurement mode, however, is small enough to be allowable in normal use, and thus there is no problem with the simultaneous measurement mode in general use.

The NH$_3$ concentration map is required to be used to calculate the NOx concentration also in the switching measurement mode. In the above-mentioned case, however, the electromotive force EMF occurring in the mixed potential cell 61 is not measured during measurement of the pump current Ip2, and thus the NOx concentration is corrected based on the $NH_3$ concentration obtained most recently when the NOx concentration is obtained. Thus, long time intervals between measurement of the electromotive force EMF performed by the $NH_3$ sensor part and measurement of the pump current Ip2 performed by the NOx sensor part are undesirable because the concentration in the measurement gas can vary between the measurements, correction is not suitable for the measurement gas when the pump current Ip2 is measured, and, as a result, the NOx concentration cannot correctly be obtained. It is preferable to perform switching at time intervals of 100 msec or shorter from this viewpoint.

In the case of the gas sensor 100 according to the present embodiment, measurement of the electromotive force EMF using the $NH_3$ sensor part and measurement of the pump current Ip2 using the NOx sensor part are performed at the same element control temperature, and thus switching can be performed at such short time intervals.

Measurement in the switching measurement mode is suitable for a case where the gas sensor 100 is used to control injection of urea with high precision in a urea SCR system, for example.

Selective Measurement Mode

As an application of the above-mentioned switching measurement mode, measurement of the electromotive force EMF for obtaining the $NH_3$ concentration can be performed by the $NH_3$ sensor part in the state of suspending control of the NOx sensor part, while the NOx concentration can be obtained by operating both the NOx sensor part and the $NH_3$ sensor part to measure the pump current Ip2 and the electromotive force EMF simultaneously as in the simultaneous measurement mode. Such a measurement mode in which measurement for obtaining the $NH_3$ concentration and measurement for obtaining the NOx concentration are appropriately selected is referred to as a selective measurement mode.

In the selective measurement mode, similar precision is ensured for the $NH_3$ concentration to that ensured in the switching measurement mode. On the other hand, the electromotive force EMF and the pump current Ip2 required to obtain the NOx concentration are measured simultaneously in contrast to the switching measurement mode, so that no problem is caused by correction of the NOx concentration even when switching interval is not limited to 100 msec or shorter. The value of the NOx concentration derived from the pump current Ip2 is not affected by the electromotive force EMF in the mixed potential cell 61 measured simultaneously with the pump current Ip2.

Measurement in the selective measurement mode is suitable for a case where the $NH_3$ concentration and the NOx concentration are not always required to be obtained in parallel or while continually performing switching. Examples of the application include a case where one of the $NH_3$ concentration and the NOx concentration is required to be routinely obtained, while the other one of the $NH_3$ concentration and the NOx concentration is obtained only at a predetermined timing or only when necessary. Also in this case, there is no need to switch the element control temperature, as well as in the switching measurement mode. This means that transition (switching) between measurement of the electromotive force EMF for obtaining the $NH_3$ concentration and simultaneous measurement of the pump current Ip2 and the electromotive force EMF for obtaining the NOx concentration can be performed at short time intervals of 100 msec or shorter, which is similar to the time intervals at which switching is performed in the switching measurement mode.

The simultaneous measurement mode, the switching measurement mode, and the selective measurement mode may be used appropriately in accordance with the use aspect of the gas sensor 100, and the mode to be used may be switched at an appropriate timing. It is needless to say that the element control temperature is not required to be switched when the mode is switched, and thus time required for switching is extremely short.

As described above, in the present embodiment, the sensor element of the gas sensor includes the NOx sensor part functioning as a limiting current NOx sensor and the $NH_3$ sensor part functioning as a mixed potential $NH_3$ sensor. In addition, an electrode functioning as the outer pump electrode in the NOx sensor part is provided as a cermet electrode formed of zirconia and a Pt-Au alloy having an Au abundance ratio of 0.25 or more and 2.30 or less to be also used as a sensing electrode for generating a mixed potential in the $NH_3$ sensor part, and the reference electrode is shared by the NOx sensor part and the $NH_3$ sensor part. Furthermore, each pump cell in the NOx sensor part is configured to suitably operate at the element control temperature of 400° C. or higher and 600° C. or lower, which is lower than the temperature at which the solid electrolytes included in the sensor element demonstrate favorable oxygen ion conductivity, by increasing the front-end diffusion resistance provided to the measurement gas flowing through the gas inlet and reaching the first internal space to limit the amount of the measurement gas reaching the first internal space. According to the present embodiment, a gas sensor (multi-gas sensor) functioning as the $NH_3$ sensor and as the NOx sensor at the same element control temperature is achieved without complicating the configuration of the conventional NOx sensor.

The gas sensor can perform three measurement modes, namely, the simultaneous measurement mode in which NOx and $NH_3$ in the measurement gas are measured simultaneously, the switching measurement mode in which measurement of NOx in the NOx sensor part and measurement of $NH_3$ in the $NH_3$ sensor part are performed while being switched, and the selective measurement mode in which measurement for obtaining the $NH_3$ concentration and measurement for obtaining the NOx concentration are appropriately selected, and the measurement mode to be used can be switched in accordance with the use aspect. There is no need to change the element control temperature, and thus switching in the switching measurement mode and in the selective measurement mode and switching among the modes can be performed at short time intervals of 100 msec or shorter, for example.

While the invention has been shown and described in detail, the foregoing description is in all aspects illustrative and not restrictive. It is therefore understood that numerous modifications and variations can be devised without departing from the scope of the invention.

What is claimed is:

1. A gas sensor for detecting a predetermined gas component in a measurement gas, said gas sensor comprising:
    a sensor element including a lamination of a plurality of oxygen-ion conductive solid electrolyte layers; and
    a heater located inside said sensor element to heat said sensor element, wherein said sensor element includes:
        a NOx sensor part; and
        a $NH_3$ sensor part,
    said NOx sensor part includes:

a gas inlet through which said measurement gas is introduced from an external space;

at least one internal space into which said measurement gas is introduced;

a front-end diffusion resistance providing part located between said external space and said at least one internal space to provide a diffusion resistance of 0.90 (1/mm) or higher and 6.00 (1/mm) or lower to said measurement gas;

a NOx measurement electrode formed to face said at least one internal space;

an outer pump electrode formed on a surface of said sensor element; and a reference electrode located between two of said plurality of oxygen-ion conductive solid electrolyte layers to be in contact with a reference gas, said NOx sensor part has a measurement pump cell that is an electrochemical pump cell constituted by said NOx measurement electrode, said outer pump electrode, and a solid electrolyte between said NOx measurement electrode and said outer pump electrode, said $NH_3$ sensor part has a mixed potential cell constituted by said outer pump electrode, said reference electrode, and a solid electrolyte between said outer pump electrode and said reference electrode, said outer pump electrode having catalytic activity inactivated for $NH_3$, and said gas sensor is configured to be, in a state in which said heater heats said sensor element to an element control temperature of 400° C. or higher and 600° C. or lower, capable of simultaneously in parallel or selectively performing:

determination of a $NH_3$ concentration based on a potential difference occurring between said outer pump electrode and said reference electrode in said mixed potential cell; and determination of a NOx concentration in said measurement gas based on said $NH_3$ concentration and a pump current flowing between said NOx measurement electrode and said outer pump electrode in a state of controlling a voltage applied across said NOx measurement electrode and said outer pump electrode to maintain a potential difference between said NOx measurement electrode and said reference electrode constant.

2. The gas sensor according to claim 1, wherein
said outer pump electrode is formed of a cermet composed of a noble metal and an oxygen-ion conductive solid electrolyte, and
said noble metal is a Pt—Au alloy, and an Au abundance ratio is 0.25 or more and 2.30 or less, said Au abundance ratio being an area ratio of a portion covered with Au to a portion at which Pt is exposed in a surface of noble metal particles included in said outer pump electrode.

3. The gas sensor according to claim 1, wherein
measurement of said potential difference for determination of said $NH_3$ concentration and measurement of said pump current for determination of said NOx concentration are performed while being switched at time intervals of 100 msec or shorter, and said measurement pump cell is suspended during measurement of said potential difference.

4. The gas sensor according to claim 1, wherein
measurement of said potential difference for determination of said $NH_3$ concentration and measurement of said pump current for determination of said NOx concentration are capable of being selectively performed at any timing, and said measurement pump cell is suspended during measurement of said potential difference.

5. The gas sensor according to claim 1, wherein
said at least one internal space comprises a first internal space and a second internal space,
said NOx measurement electrode is located inside said second internal space, and has NOx reducing ability,
said NOx sensor part further includes:
an inner pump electrode formed to face said first internal space; and
an auxiliary pump electrode formed to face said second internal space,
said front-end diffusion resistance providing part is a part from said external space until said first internal space,
said first internal space and said second internal space communicate with each other via a diffusion control part providing a predetermined diffusion resistance to said measurement gas,
said NOx sensor part has:
a main pump cell constituted by said inner pump electrode, said outer pump electrode, and a solid electrolyte between said inner pump electrode and said outer pump electrode, and pumping in or pumping out oxygen between said first internal space and said external space; and
an auxiliary pump cell that is an electrochemical pump cell constituted by said auxiliary pump electrode, said outer pump electrode, and a solid electrolyte between said auxiliary pump electrode and said outer pump electrode, and pumping out oxygen from said second internal space to said external space, and
said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

6. The gas sensor according to claim 2, wherein
measurement of said potential difference for determination of said $NH_3$ concentration and measurement of said pump current for determination of said NOx concentration are performed while being switched at time intervals of 100 msec or shorter, and said measurement pump cell is suspended during measurement of said potential difference.

7. The gas sensor according to claim 2, wherein
measurement of said potential difference for determination of said $NH_3$ concentration and measurement of said pump current for determination of said NOx concentration are capable of being selectively performed at any timing, and said measurement pump cell is suspended during measurement of said potential difference.

8. The gas sensor according to claim 2, wherein
said at least one internal space comprises a first internal space and a second internal space,
said NOx measurement electrode is located inside said second internal space, and has NOx reducing ability,
said NOx sensor part further includes:
an inner pump electrode formed to face said first internal space; and
an auxiliary pump electrode formed to face said second internal space, said front-end diffusion resistance providing part is a part from said external space until said first internal space,
said first internal space and said second internal space communicate with each other via a diffusion control part providing a predetermined diffusion resistance to said measurement gas,
said NOx sensor part has:
 a main pump cell constituted by said inner pump electrode, said outer pump electrode, and a solid electrolyte between said inner pump electrode and said outer pump electrode, and pumping in or pumping out oxygen between said first internal space and said external space; and
 an auxiliary pump cell that is an electrochemical pump cell constituted by said auxiliary pump electrode, said outer pump electrode, and a solid electrolyte between said auxiliary pump electrode and said outer pump electrode, and pumping out oxygen from said second internal space to said external space, and
said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

9. The gas sensor according to claim 3, wherein
said at least one internal space comprises a first internal space and a second internal space,
said NOx measurement electrode is located inside said second internal space, and has NOx reducing ability,
said NOx sensor part further includes:
 an inner pump electrode formed to face said first internal space; and
 an auxiliary pump electrode formed to face said second internal space,
said front-end diffusion resistance providing part is a part from said external space until said first internal space,
said first internal space and said second internal space communicate with each other via a diffusion control part providing a predetermined diffusion resistance to said measurement gas,
said NOx sensor part has:
 a main pump cell constituted by said inner pump electrode, said outer pump electrode, and a solid electrolyte between said inner pump electrode and said outer pump electrode, and pumping in or pumping out oxygen between said first internal space and said external space; and
 an auxiliary pump cell that is an electrochemical pump cell constituted by said auxiliary pump electrode, said outer pump electrode, and a solid electrolyte between said auxiliary pump electrode and said outer pump electrode, and pumping out oxygen from said second internal space to said external space, and
said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

10. The gas sensor according to claim 4, wherein
said at least one internal space comprises a first internal space and a second internal space,
said NOx measurement electrode is located inside said second internal space, and has NOx reducing ability,
said NOx sensor part further includes:
 an inner pump electrode formed to face said first internal space; and
 an auxiliary pump electrode formed to face said second internal space,
said front-end diffusion resistance providing part is a part from said external space until said first internal space,
said first internal space and said second internal space communicate with each other via a diffusion control part providing a predetermined diffusion resistance to said measurement gas,
said NOx sensor part has:
 a main pump cell constituted by said inner pump electrode, said outer pump electrode, and a solid electrolyte between said inner pump electrode and said outer pump electrode, and pumping in or pumping out oxygen between said first internal space and said external space; and
 an auxiliary pump cell that is an electrochemical pump cell constituted by said auxiliary pump electrode, said outer pump electrode, and a solid electrolyte between said auxiliary pump electrode and said outer pump electrode, and pumping out oxygen from said second internal space to said external space, and
said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

11. The gas sensor according to claim 6, wherein
said at least one internal space comprises a first internal space and a second internal space,
said NOx measurement electrode is located inside said second internal space, and has NOx reducing ability,
said NOx sensor part further includes:
 an inner pump electrode formed to face said first internal space; and
 an auxiliary pump electrode formed to face said second internal space,
said front-end diffusion resistance providing part is a part from said external space until said first internal space,
said first internal space and said second internal space communicate with each other via a diffusion control part providing a predetermined diffusion resistance to said measurement gas,
said NOx sensor part has:
 a main pump cell constituted by said inner pump electrode, said outer pump electrode, and a solid electrolyte between said inner pump electrode and said outer pump electrode, and pumping in or pumping out oxygen between said first internal space and said external space; and
 an auxiliary pump cell that is an electrochemical pump cell constituted by said auxiliary pump electrode, said outer pump electrode, and a solid electrolyte between said auxiliary pump electrode and said outer pump electrode, and pumping out oxygen from said second internal space to said external space, and
said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

12. The gas sensor according to claim 7, wherein
said at least one internal space comprises a first internal space and a second internal space,
said NOx measurement electrode is located inside said second internal space, and has NOx reducing ability,
said NOx sensor part further includes:
  an inner pump electrode formed to face said first internal space; and
  an auxiliary pump electrode formed to face said second internal space,
said front-end diffusion resistance providing part is a part from said external space until said first internal space,
said first internal space and said second internal space communicate with each other via a diffusion control part providing a predetermined diffusion resistance to said measurement gas,
said NOx sensor part has:
  a main pump cell constituted by said inner pump electrode, said outer pump electrode, and a solid electrolyte between said inner pump electrode and said outer pump electrode, and pumping in or pumping out oxygen between said first internal space and said external space; and
  an auxiliary pump cell that is an electrochemical pump cell constituted by said auxiliary pump electrode, said outer pump electrode, and a solid electrolyte between said auxiliary pump electrode and said outer pump electrode, and pumping out oxygen from said second internal space to said external space, and
said measurement pump cell pumps out oxygen generated by reducing, with said NOx measurement electrode, NOx in said measurement gas having oxygen partial pressure controlled by said main pump cell and said auxiliary pump cell, thereby allowing said pump current to flow between said NOx measurement electrode and said outer pump electrode.

* * * * *